United States Patent
Saxer et al.

(10) Patent No.: US 10,409,046 B2
(45) Date of Patent: Sep. 10, 2019

(54) ILLUMINATION FIELD DIAPHRAGMS FOR USE IN MICROSCOPES AND RELATED METHODS AND SYSTEMS

(71) Applicant: Bioptigen, Inc., Morrisville, NC (US)

(72) Inventors: Christopher Saxer, Cary, NC (US); Al-Hafeez Z. Dhalla, Durham, NC (US); Robert H. Hart, Cary, NC (US); Eric L. Buckland, Hickory, NC (US)

(73) Assignee: Bioptigen, Inc., Morrisville, NC (US)

( * ) Notice: Subject to any disclaimer, the term of this patent is extended or adjusted under 35 U.S.C. 154(b) by 0 days.

(21) Appl. No.: 14/935,545

(22) Filed: Nov. 9, 2015

(65) Prior Publication Data

US 2017/0131533 A1 May 11, 2017

(51) Int. Cl.
*G02B 21/00* (2006.01)
*G02B 21/06* (2006.01)
(Continued)

(52) U.S. Cl.
CPC .......... *G02B 21/0012* (2013.01); *A61B 3/102* (2013.01); *A61B 3/12* (2013.01);
(Continued)

(58) Field of Classification Search
CPC ............... G02B 21/00; G02B 21/0012; G02B 21/0032; G02B 21/0052; G02B 21/06; G02B 21/08; G02B 21/10; G02B 21/02; G02B 7/00; G02B 7/006; G02B 27/00; G02B 27/0018; G02B 27/0075; G02B 27/09
See application file for complete search history.

(56) References Cited

U.S. PATENT DOCUMENTS 4,407,569 A * 10/1983 Piller .................. G02B 21/08
359/370
5,136,429 A 8/1992 Bergner et al.
(Continued)

FOREIGN PATENT DOCUMENTS

DE 10 2007 005 790 A1 8/2008
DE 10 2007 041 003 A1 12/2008

OTHER PUBLICATIONS

Invitation to Pay Additional Fees and, Where Applicable, Protest Fee, and Communication Related to the Results of the Partial International Search, PCT/US2016/060497, dated Feb. 16, 2017, 6 pages.
(Continued)

*Primary Examiner* — Thong Q Nguyen
(74) *Attorney, Agent, or Firm* — Stanek Lemon Crouse & Meeks, PA

(57) ABSTRACT

Field diaphragms for use in surgical microscopes are provided. The field diaphragms are positioned along an optical axis of a microscope illumination system. The field diaphragms include a frame portion configured to be received by the surgical microscope; and a non-circularly symmetric mask portion integrated with the frame portion. The mask portion is aligned such that marginal rays from an edge of the field diaphragm along a meridian of minimum diameter that reflect from a surface of an objective lens of the microscope reflect outside of an acceptance angle for relay through any ocular channel of the microscope.

8 Claims, 9 Drawing Sheets

(51) Int. Cl.

| | |
|---|---|
| *G02B 27/00* | (2006.01) |
| *G02B 5/00* | (2006.01) |
| *G02B 7/00* | (2006.01) |
| *G02B 21/02* | (2006.01) |
| *G02B 21/22* | (2006.01) |
| *A61B 3/12* | (2006.01) |
| *A61B 3/10* | (2006.01) |
| *G02B 21/08* | (2006.01) |

(52) U.S. Cl.
CPC ............ *A61B 3/1225* (2013.01); *G02B 5/005* (2013.01); *G02B 7/006* (2013.01); *G02B 21/02* (2013.01); *G02B 21/06* (2013.01); *G02B 21/082* (2013.01); *G02B 21/22* (2013.01); *G02B 27/0018* (2013.01)

(56) References Cited

U.S. PATENT DOCUMENTS

| | | | | |
|---|---|---|---|---|
| 6,891,671 B1* | 5/2005 | Greenberg | ......... | G02B 21/0004 359/368 |
| 7,889,423 B2 | 2/2011 | Reimer et al. | | |
| 7,907,336 B2* | 3/2011 | Abele | ...................... | A61B 3/13 359/385 |
| 8,023,184 B2* | 9/2011 | Weber | .................... | G02B 21/06 359/368 |
| 8,031,399 B2 | 10/2011 | Sander | | |
| 8,576,483 B2 | 11/2013 | Tanabe et al. | | |
| 2012/0162602 A1 | 6/2012 | Huening et al. | | |
| 2013/0321609 A1* | 12/2013 | Seitz | .................. | G02B 21/0016 348/79 |
| 2016/0306155 A1* | 10/2016 | Suzuki | ................... | G02B 21/26 |

OTHER PUBLICATIONS

Notification of Transmittal of the International Search Report and the Written Opinion of the International Searching Authority, or the Declaration, PCT/US2016/060497, dated May 26, 2017, 16 pages.
Notification Concerning Transmittal of International Preliminary Report on Patentability, PCT/US2016/060497, dated May 24, 2018, 11 pages.

* cited by examiner

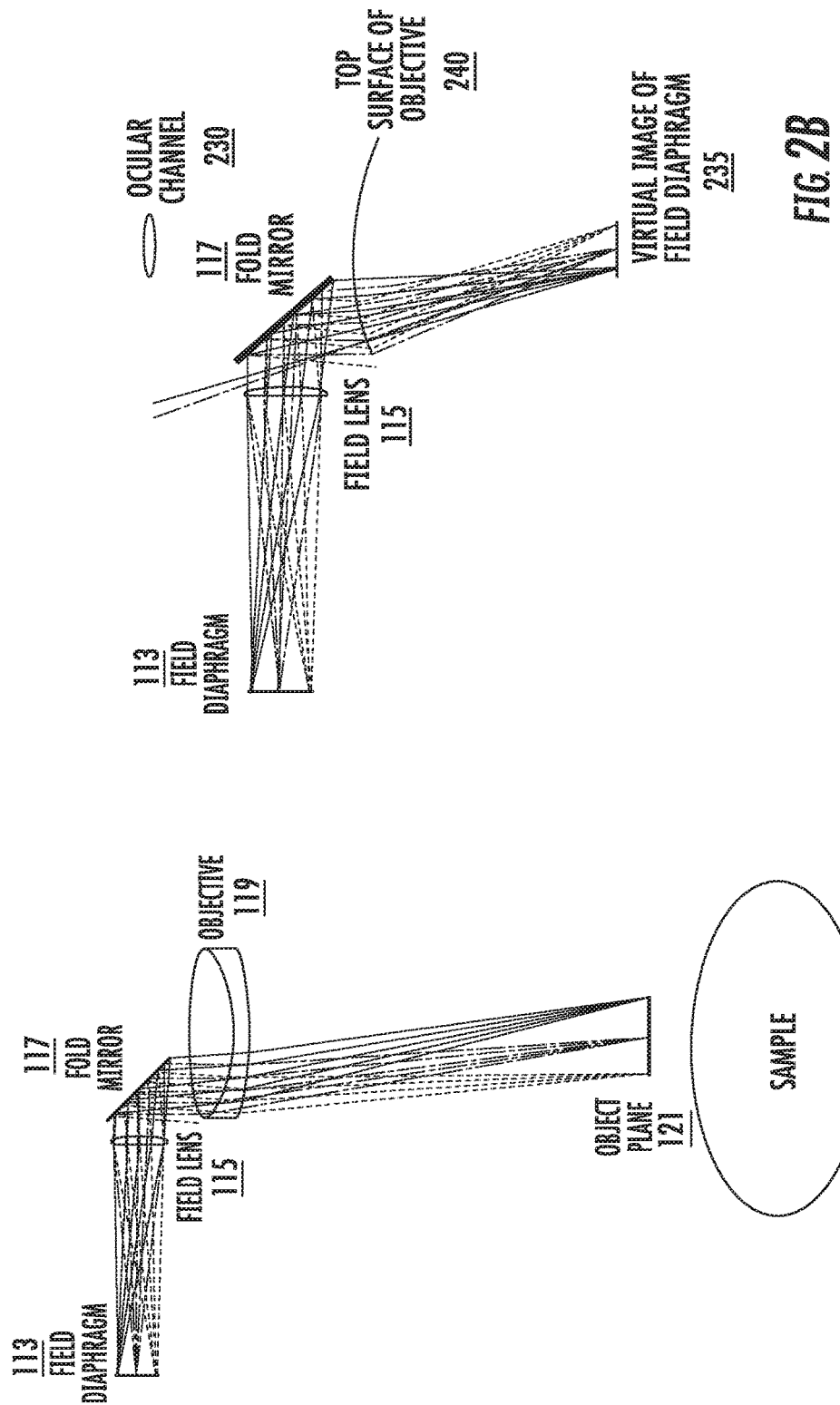

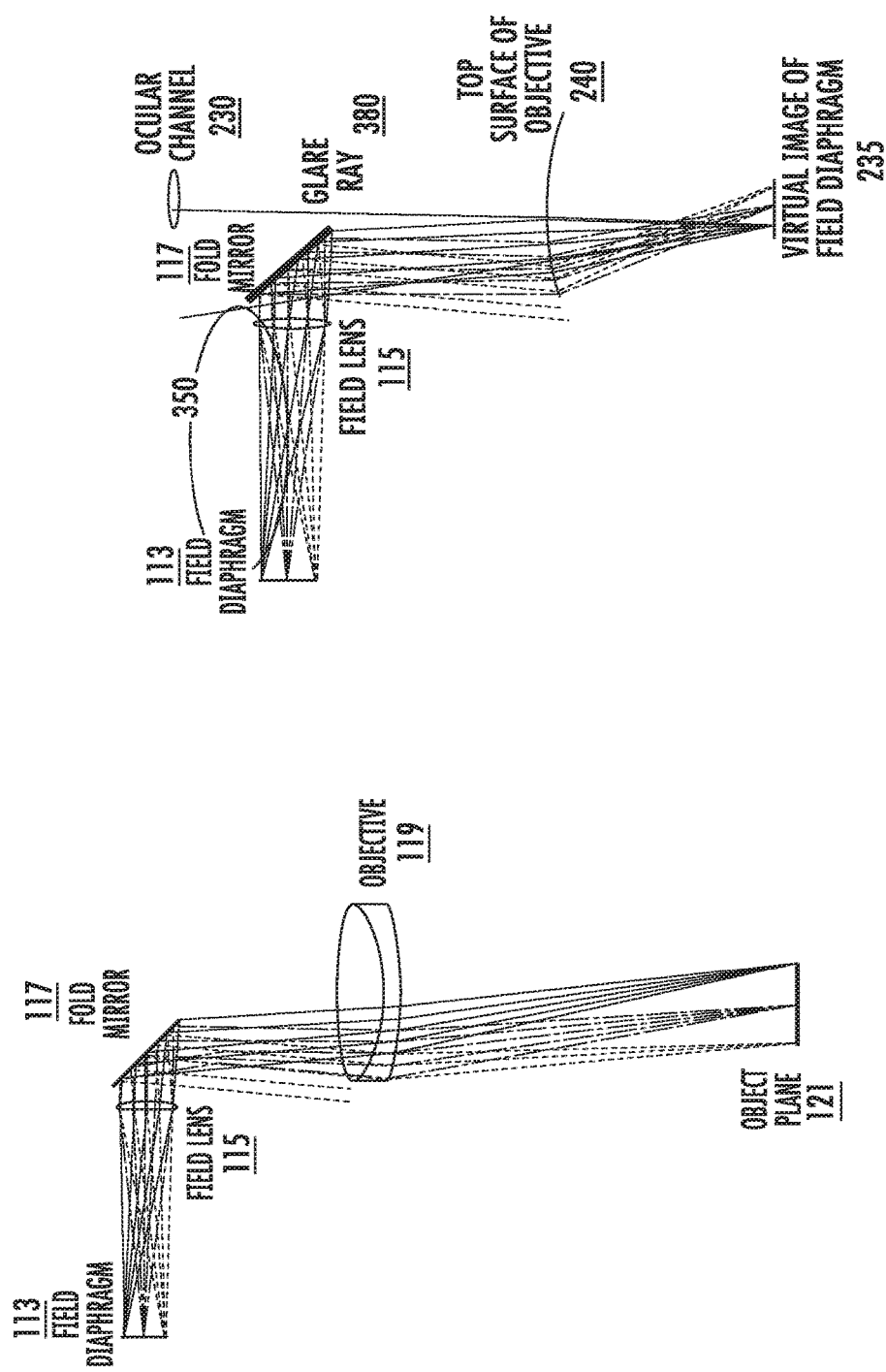

ILLUMINATION FIELD DIAPHRAGMS FOR USE IN MICROSCOPES AND RELATED METHODS AND SYSTEMS

FIELD

The present inventive concept relates generally to surgical microscopes and, more particularly, to methods, systems and devices for compensating for illumination glare in the field of view of a surgical microscope.

BACKGROUND

Generally, common main objective (CMO) surgical microscopes use vertical illumination that is projected down onto a sample, nearly parallel to an observer's viewing angle. In these microscopes, glare may occur when light from the vertical illumination reflects off one surface of the microscope objective lens and couples into one of the ocular channels.

These microscopes are typically designed to reduce, or possibly prevent, reflected rays from reaching or coupling into the microscope ocular channels, thereby reducing, or possibly avoiding, glare. A combination of techniques have been used to reduce the likelihood of glare, for example, high quality coatings may be used to reduce reflection intensity; location of virtual images may be controlled by careful choice of lens curvatures and spacing; field diaphragms and baffles may be used to block reflected light that does not contribute to the microscope image and the like.

SUMMARY

Some embodiments of the present inventive concept provide field diaphragms for use in a surgical microscope. The field diaphragm is positioned along an optical axis of a microscope illumination system. The field diaphragm includes a frame portion configured to be received by the surgical microscope; and a non-circularly symmetric mask portion integrated with the frame portion. The mask portion is aligned such that marginal rays from an edge of the field diaphragm along a meridian of minimum diameter that reflect from a surface of an objective lens of the microscope reflect outside of an acceptance angle for relay through any ocular channel of the microscope.

In further embodiments, the mask portion may include a circularly symmetric diaphragm of a maximum clear aperture with a non-circularly symmetric inset obscuration restricting the clear aperture along at least one meridian.

In still further embodiments, the inset obscuration may include a rectangular obscuration mask being about 8 mm wide and located about 9.5 mm from a center of an aperture and about twenty degrees from vertical.

In some embodiments, the mask portion may be configured to be received by a filter slot in the surgical microscope.

In further embodiments, the surgical microscope may include an accessory in an infinity space of the surgical microscope. The presence of the accessory may alter a glare management system of the surgical microscope by displacing a position of an objective lens of the surgical microscope.

In still further embodiments, the mask portion may be configured to block portions of the illumination beam to reduce back reflections from the displaced objective lens.

Some embodiments of the present inventive concept provide systems for controlling glare in oculars of a surgical microscope. The system includes a surgical microscope; and a non-circularly symmetric field diaphragm configured to be received by the surgical microscope. The field diaphragm is configured to block portions of an illumination beam of the surgical microscope to reduce regions of glare in a field of view (FOV) of the microscope visible through oculars thereof.

In further embodiments, the surgical microscope may further include an objective lens and an infinity space above the objective lens. The infinity space may be configured to receive an accessory therein and the presence of the accessory may alter a glare management system of the surgical microscope by displacing the position of the objective lens of the surgical microscope.

In still further embodiments, the field diaphragm may be configured to block portions of the illumination beam to reduce back reflections from the displaced objective lens.

In some embodiments, the accessory may be an optical coherence tomography (OCT) accessory.

In further embodiments, the field diaphragm may include a circularly symmetric diaphragm of a maximum clear aperture with a non-circularly symmetric inset obscuration restricting the clear aperture along at least one meridian.

In still further embodiments, the inset obscuration may be a rectangular obscuration mask being about 8 mm wide and located about 9.5 mm from a center of an aperture and about twenty degrees from vertical.

In some embodiments, the surgical microscope may further include a filter slot. The filter slot may be configured to receive the glare mask.

In further embodiments, the field diaphragm may include a frame portion configured to be received by the surgical microscope; and a mask portion integrated with the frame portion, the mask portion configured to block portions of the illumination beam of the surgical microscope.

Still further embodiments of the present inventive concept provide a surgical microscope including at least one ocular; an objective lens optically coupled to the at least one ocular; a collimated space between the at least one ocular and the objective lens, wherein the collimated space is configured to receive an optical accessory therein and wherein the optical accessory is optically coupled to an imaging path of the surgical microscope; an illumination system optically coupled into the collimated space of the surgical microscope, wherein an illumination from the illumination system is directed along a path at least partially contained within the collimated space of the surgical microscope and through the objective lens; and one of a field diaphragm and obscuration mask positioned within the illumination system, and outside of a field of view of the at least one oculars, wherein the one of the field diaphragm and the obscuration mask blocks, attenuates or diverts rays from the illumination system that reflect from a surface of the objective lens such that the reflected rays are not visible through the at least one ocular.

In some embodiments, one of a first field diaphragm and first obscuration mask may be positioned within the path of the illumination system when the surgical microscope is operated without the optical accessory coupled to the imaging path of the microscope. One of a second field diaphragm and a second obscuration mask may be positioned within the path of the illumination system when the surgical microscope is operated with the optical accessory coupled to the imaging path of the microscope.

In further embodiments, the position of the objective lens, when the surgical microscope is operated with the optical accessory coupled to imaging path of the microscope, may be displaced a distance dL along the optical axis of the objective lens relative to the axial position of the objective lens when the surgical microscope is operated without the optical accessory coupled to imaging path of the microscope.

In still further embodiments, a radial dimension of the one of the second field diaphragm and the second obscuration mask may be de-magnified relative to a radial dimension of the first field diaphragm by an approximate ratio $R=[1-(M-1)*dL/(L\_0+FL)]$, where M is the magnification of the first field diaphragm at the image plane, and $L\_0+FL$ is the sum of path lengths from a first field diaphragm to a first objective lens position $L\_0$ and a focal length of the objective lens FL.

In some embodiments, the accessory may include one of an optical coherence tomography (OCT) device, a scanning laser ophthalmoscope device, wavefront analysis device, an autorefractor device, a video camera, and a laser delivery device.

In further embodiments, the one of the second field diaphragm and the second obscuration mask is non-circularly symmetric.

In still further embodiments, the one of the second field diaphragm and the second obscuration mask is circularly symmetric.

BRIEF DESCRIPTION OF THE DRAWINGS

FIGS. 2A and 2B are schematic representations of an illumination system of a microscope using vertical illumination where the illumination rays reach an object plane (2A) and where the virtual image of the field diaphragm formed by reflection off of the top surface of the objective is obscured from the ocular channel (2B).

FIGS. 3A and 3B are schematic representations of an illumination system of a microscope including an accessory in the infinity space of the microscope where the illumination rays reach an object plane (3A) and where the virtual image of the field diaphragm formed by reflection off of the top surface of the objective lens produces a glare (3B).

DETAILED DESCRIPTION

Figure 1:
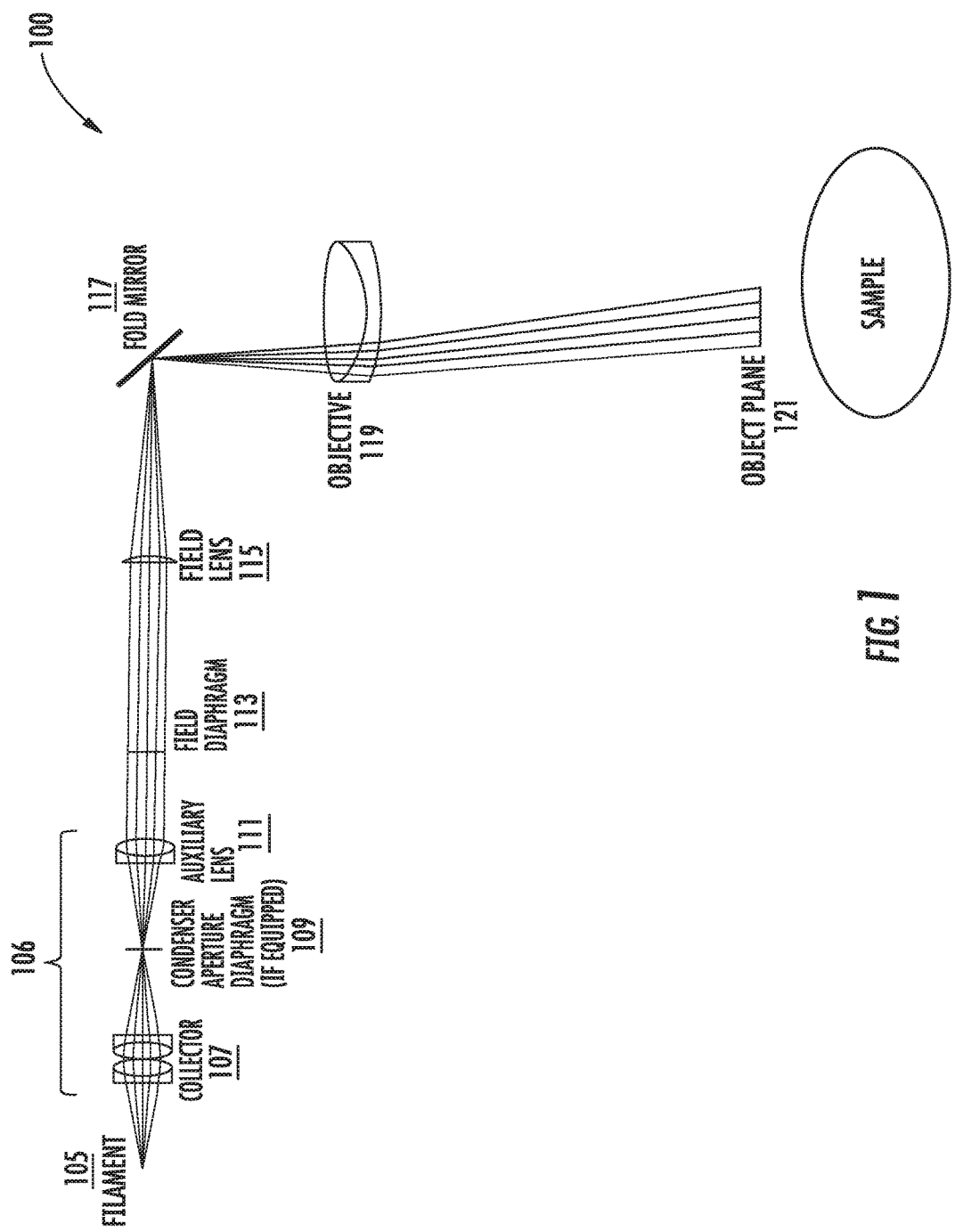
FIG. 1 is a schematic diagram of a surgical microscope with vertical illumination.

The present inventive concept will be described more fully hereinafter with reference to the accompanying figures, in which embodiments of the inventive concept are shown. This inventive concept may, however, be embodied in many alternate forms and should not be construed as limited to the embodiments set forth herein.

Accordingly, while the inventive concept is susceptible to various modifications and alternative forms, specific embodiments thereof are shown by way of example in the drawings and will herein be described in detail. It should be understood, however, that there is no intent to limit the inventive concept to the particular forms disclosed, but on the contrary, the inventive concept is to cover all modifications, equivalents, and alternatives falling within the spirit and scope of the inventive concept as defined by the claims. Like numbers refer to like elements throughout the description of the figures.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises", "comprising," "includes" and/or "including" when used in this specification, specify the presence of stated features, integers, steps, operations, elements, and/or components, but do not preclude the presence or addition of one or more other features, integers, steps, operations, elements, components, and/or groups thereof. Moreover, when an element is referred to as being "responsive" or "connected" to another element, it can be directly responsive or connected to the other element, or intervening elements may be present. In contrast, when an element is referred to as being "directly responsive" or "directly connected" to another element, there are no intervening elements present. As used herein the term "and/or" includes any and all combinations of one or more of the associated listed items and may be abbreviated as "/".

Unless otherwise defined, all terms (including technical and scientific terms) used herein have the same meaning as commonly understood by one of ordinary skill in the art to which this inventive concept belongs. It will be further understood that terms used herein should be interpreted as having a meaning that is consistent with their meaning in the context of this specification and the relevant art and will not be interpreted in an idealized or overly formal sense unless expressly so defined herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure. Although some of the diagrams include arrows on communication paths to show a primary direction of communication, it is to be understood that communication may occur in the opposite direction to the depicted arrows.

As discussed above, surgical microscopes use vertical illumination projected down onto a sample, nearly parallel to an observer's viewing angle. In these microscopes, glare may occur when light from the vertical illumination reflects off one of the surfaces of the microscope objective and couples into one of the ocular channels. Surgical microscopes provide a magnified view of an operating field to the surgeon. Surgical microscopes are frequently of the common-main-objective stereo-zoom construction (CMO-SZM). Some surgical microscopes have binocular view ports for the surgeon, and frequently have one or two observer view ports (oculars) at ninety degrees (left and right) to the surgeon.

These microscopes typically include a wide field illumination system that includes incoherent light that is coupled into an infinity-space of the microscope, between a zoom assembly and the common main objective. This illumination is directed downward (away from the oculars) using one or more strategically placed mirrors that are not visible through the oculars. These microscopes include a field diaphragm proximate the illuminator to control the field of illumination as well as other structures designed to reduce, or possibly prevent, reflected rays from reaching or coupling into the microscope ocular channels, thereby reducing, or possibly avoiding, glare. However, when a new element of the microscope system is installed, for example, a microscope accessory, a position of a lens may be shifted and the method used to control the glare may not function properly.

In some embodiments of the present inventive concept, the accessory may be an optical coherence tomography (OCT) accessory, a filter, a video camera, a wavefront analysis system, a scanning laser ophthalmoscope, an autorefractor, a fluorescence imaging system, a therapeutic laser delivery system, or the like. In particular, such a device may be installed into the collimated, or "infinity space" of a stereo microscope. In such an installation, the objective lens is relocated from its original position and, thus may cause the specific techniques used to reduce, or possibly eliminate, glare in a particular microscope to fail, especially if these techniques are sensitive to an axial position of an objective lens. Accordingly, some embodiments of the present inventive concept provide a field diaphragm or glare mask compatible with, for example, a CMO microscope to reduce, or possibly eliminate, glare originating from a modified location of the main objective lens as will be discussed further herein with respect to FIGS. 1 through 9B.

Referring now to FIG. 1, a schematic representation of a CMO microscope, illustrated in FIG. 9A, with vertical illumination will be discussed. As illustrated in FIG. 1, the microscope illumination system 100 includes a bulb filament or an Light Emitting Diode (LED) 105, a collector lens set 107, a condenser aperture diaphragm 109, an auxiliary lens 111, a field diaphragm (FD) 113, a field lens 115, a fold mirror 117, an objective lens 119, an object plane 121 and a sample. As used herein, a sample refers to an object to be imaged, for example, a human eye. Although many of the examples discussed herein refer to the sample being an eye, specifically, the retina, cornea, anterior segment and lens of the eye, embodiments of the present inventive concept are not limited to this type of sample. Any type of sample that may be used in conjunction with embodiments discussed herein may be used without departing from the scope of the present inventive concept.

As illustrated in FIG. 1, CMO microscopes with vertical illumination typically use a Kohler illumination in a vertical (or epi-illumination) configuration. It will be understood that specific implementations of CMO microscopes vary and embodiments discussed herein are provided as examples only. As illustrated, light emitted from the bulb filament or LED 105 is gathered by a light collection system 106. As will be understood by those having skill in the art, light collection systems 106 vary and may or may not include a condenser aperture diaphragm 109 to control light intensity. For example, in embodiments without the condenser aperture diaphragm 109, light intensity can be controlled via modulation of a drive current to the bulb. However, the collection system 106 illustrated in embodiments of FIG. 1 include a collector 107, a condenser aperture diaphragm 109 and an auxiliary lens 111. Light exiting the collection system 106 is directed towards a field diaphragm 113 that is conjugate to the object plane 121. The field diaphragm 113 is then imaged onto the object plane 121 via a field lens 115, fold mirror 117 and objective lens 119. Thus, the field diaphragm 113 controls the extent of the illuminated field at the object plane 121.

Referring now to FIGS. 2A and 2B, schematic representations of an illumination system of a CMO microscope using a vertical Kohler illumination will be discussed. FIG. 2A is a schematic representation showing illumination rays reaching an object plane and FIG. 2B is a schematic representation illustrating a virtual image of the field diaphragm formed by reflection off of the top surface of the objective lens. Like reference numerals of FIGS. 2A and 2B refer to like elements illustrated with respect to FIG. 1 and will not be repeated herein in the interest of brevity.

Referring now to FIGS. 2A and 2B, the most common source of glare in CMO microscopes are reflections off of the microscope objective lens 119. FIGS. 2A and 2B illustrate a ray diagram of an optical system of a CMO microscope, but the ray diagram is simplified to be represented in two dimensions. The system illustrated in FIGS. 2A and 2B has been designed to reduce, or possibly eliminate, glare. FIG. 2A illustrates illumination rays reaching the object plane 121. FIG. 2B illustrates rays emerging from the virtual image 235 of the field diaphragm 113 are kept out of the ocular channel 230, because they are either obliquely reflected or obscured by the fold mirror 117. In other words, the virtual image 235 of the field diaphragm 113 formed by reflection off of a top surface of the objective lens 119 is obscured from the ocular channel 230, thereby reducing, or possibly eliminating, glare caused by the reflection off the objective lens.

Figures 9A, 9B:
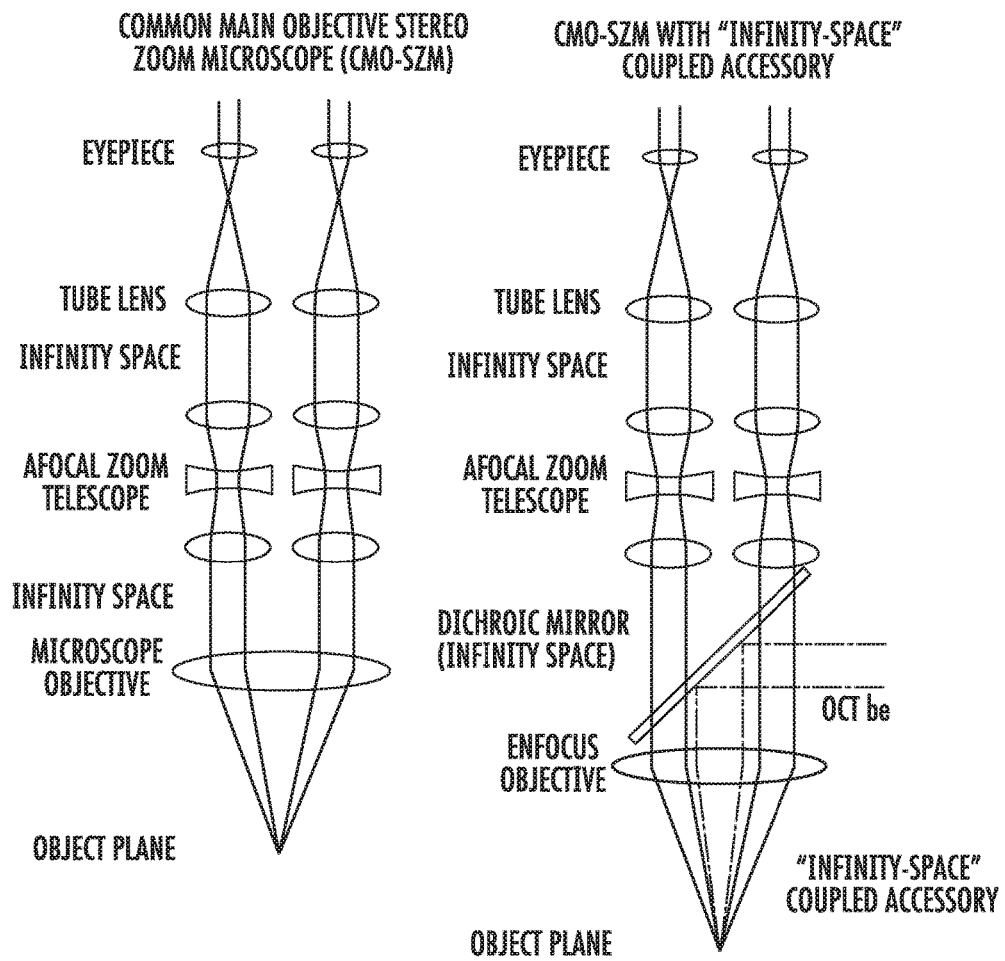
FIG. 9A is a diagram illustrating an optical path diagram of a common main objective (CMO) stereo zoom microscope (SCZ) with an objective lens in a first position in accordance with some embodiments of the present inventive concept in accordance with some embodiments of the present inventive concept.
FIG. 9B is a diagram illustrating an optical path diagram of a same CMO-SZM with an objective lens in an axially displaced second position enabling the dichroic coupling of an accessory optical device in accordance with some embodiments of the present inventive concept.

However, as discussed above, when a CMO is modified by inserting an accessory, as illustrated in FIG. 9B, the position of the objective lens may be displaced from the original position designed to reduce or eliminate glare, thus, causing the glare reduction design to be less effective or even useless. Referring now to FIGS. 3A and 3B, schematic representations of the illumination system of a CMO microscope with objective lens 119 displaced by a distance sufficient to introduce a beam splitter, for example, substantially at 45 degrees and substantially across the entire objective lens clear aperture. For example, a 45 degree beam splitter used in conjunction with a 60 mm diameter objective lens will typically require that the objective lens position be displaced 60 mm axially. Like reference numerals of FIGS. 3A and 3B refer to like elements illustrated with respect to FIGS. 1 through 2B discussed above and will not be repeated herein in the interest of brevity.

Referring now to FIGS. 3A and 3B, the microscope of FIG. 2 is modified by positioning, for example, a scan head above the objective lens 119 such that the objective lens 119 is displaced about 60 mm, lengthening the path length within the collimated, or "infinity space" of the microscope. This may occur, for example, when an OCT imaging system or the like is positioned within the infinity space of the microscope system. As illustrated in FIG. 3A, the illumination rays reach the object plane 121, virtually unchanged. However, as illustrated in FIG. 3B, the virtual image of the field diaphragm 235, formed by reflection off of a top surface of the objective lens 240, couples into the ocular channel 230, producing glare 380, which was not present before the objective lens 119 was displaced. In other words, when the objective lens 119 is displaced, the virtual image of the filament formed by the objective lens 119 is no longer obscured from the ocular channel 230. Thus, some illumination rays reflect off of the top surface of the objective lens 240 and couple into the ocular channel 230, producing glare 380.

Closer examination reveals that only rays emanating from the top of the field diaphragm 113 (350 shown in dotted circle; relative to the graphical orientation and not necessarily referring to a physical top or bottom of the microscope system) contribute to the glare. Thus, stopping down or masking the diaphragm 113 may reduce, or eliminate, the glare by blocking the stray glare-producing ray(s) 350. These glare-producing rays 350 are also present at the edge of the illuminated field. As will be discussed further herein with respect to embodiments of the present inventive concept, careful masking can reduce, or possibly eliminate, the glare with very little impact to the illumination field.

It will be understood that the systems illustrated in FIGS. 1 through 3B have been simplified to a two-dimensional representation for simplicity and, thus, do not convey the circumferential extent of the rays that create glare. In practice, only a small portion of the circumference of the field diaphragm 113 needs to be blocked to reduce or eliminate glare. As will be discussed below, this can be achieved by placing a new field diaphragm, or mask, adjacent to the original field diaphragm 113. This mask reduces, or possibly eliminates, glare while having only very little impact on the illuminated field-of-view (FOV).

Figure 4B:
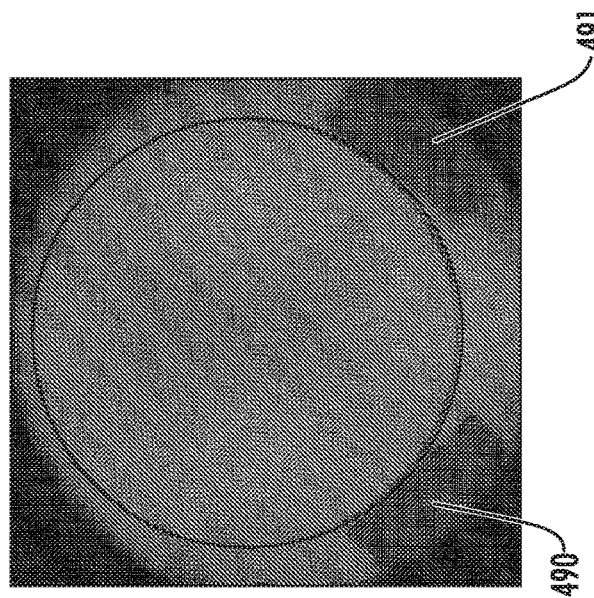
FIGS. 4A and 4B are diagrams of an illuminated field-of-view (FOV) of a Leica M844 with an accessory (4A) and an accessory and a glare mask (4B).
Figure 4A:
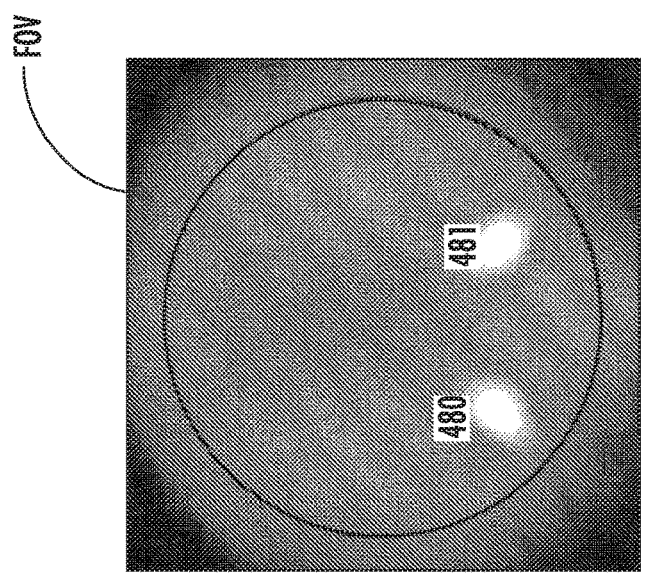

Referring now to FIGS. 4A and 4B, an illuminated FOV with and without a glare mask in accordance with embodiments discussed herein will be discussed. FIGS. 4A and 4B are images acquired through one of the assistant oculars (the ocular with the largest amount of glare) with an OCT device or the like installed, thus, displacing the objective lens and interfering with the mechanism for reducing glare as discussed above. FIG. 4A is an image acquired from a test microscope when a main objective lens is displaced 60 mm required for the installation of a dichroically coupled accessory is installed without a glare mask. As illustrated in FIG. 4A, with the objective lens axially displaced, two bright glare hotspots 480 and 481 are observed in the FOV. As illustrated in FIG. 4B, when a field diaphragm mask (glare mask) is then installed, glare has been completely eliminated by the mask in the FOV. As illustrated in FIG. 4B, the mask may cast shadows in bottom portions of the FOV. The size and shape of the shadows depends on the size and shape of the mask. The mask used to produce the image of FIG. 4B cast two small partial shadows 490 and 491 in the bottom corners of the FOV, towards the user of the microscope. In an ophthalmic surgery application with a typical microscope, these small shadows will be positioned nominally superior with respect to the head of the patient, at or above the brow, substantially out of the useable field of view of the surgeon and, thus, are potentially less disruptive to the surgical visualization than the two bright spots 480 and 481 illustrated in FIG. 4A. The images in FIGS. 4A and 4B were obtained with a Leica M844 surgical microscope. To provide scale, the circle in each image is 36 mm in diameter, three times the diameter of a cornea of an eye and 50% greater than the nasal-temporal width of an eyelid. Thus, embodiments of the present inventive concept may be used to reduce, or possibly eliminate, glare when a device is installed in a microscope that alters the original configuration of the microscope. For example, embodiments of the present inventive concept may be used to reduce or eliminate glare produced from installing an EnFocus™ Optical Coherence Tomography device on a Leica M844 surgical microscope, installing an EnFocus™ Optical Coherence Tomography device on another common main objective microscope, or installing another like accessory on a like common main objective microscope.

Surgical microscopes in accordance with some embodiments of the present inventive concept include an "infinity space." This is a space above the final objective lens. Surgical microscopes, for example, a Leica M844 surgical microscope, provide the ability to add accessories to the "infinity space" of the microscope. Accessories may include the accessories mentioned above or may include, but are not limited to, for example, a filter, a video camera, wavefront analysis system, a scanning laser ophthalmoscope, an autorefractor, a fluorescence imaging system, a therapeutic laser delivery system, or the like. The addition of an accessory, for example, an optical coherence tomography (OCT) accessory, to the infinity space of a common main objective microscope alters the glare management strategy for the microscope illumination system as discussed above.

Thus, a glare mask in accordance with embodiments discussed herein may be used to block a specific area of the main illumination beam in order to reduce, or possibly eliminate, back reflections from the displaced main objective lens (displaced by the accessory) which is observed as regions of glare in the oculars as discussed above. Some embodiments of the present inventive concept provide glare masks configured to be received by a filter slot of the microscope as will be discussed further with respect to FIGS. 5A through 8E.

Figure 5A:
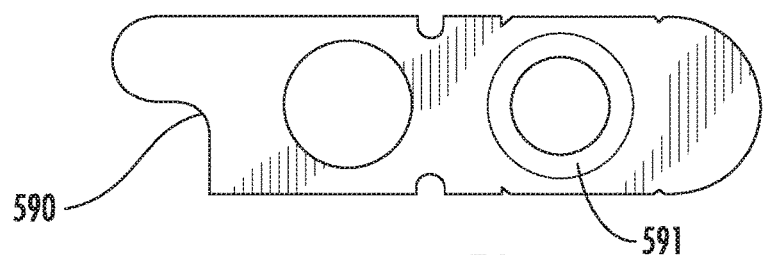
FIGS. 5A through 5C are images of various form factors of glare-reducing field diaphragms in accordance with some embodiments of the present inventive concept.
Figure 5B:
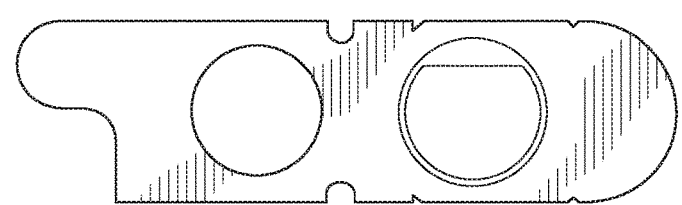
Figure 5C:
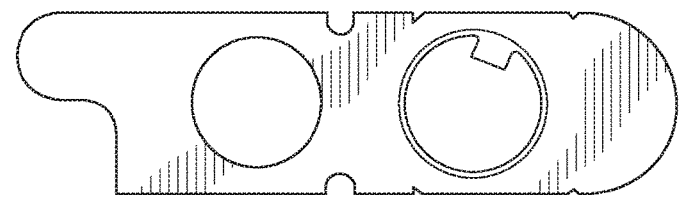

As discussed above, only some of the reflected rays are reflected back into the oculars used by the surgeon, so only some of the rays need to be blocked by the glare mask. Thus, the glare mask may have many form factors and still serve the purpose of blocking these particular rays. Referring now to FIGS. 5A through 5C, three different embodiments of a glare mask in accordance with some embodiments of the present inventive concept will be discussed. The design types illustrated in FIGS. 5A through 5C effectively reduce or eliminate glare from all ocular ports, for example, four ocular ports of the test microscope, the Leica M844. Each of the masks in FIGS. 5A through 5C has a frame portion 590 and a mask portion 591. FIG. 5A illustrates a circle obscuration mask having a diameter of 21.5 mm. FIG. 5B illustrates a straight obscuration mask perpendicular to a radius of the circumscribed aperture at a radial distance 10 mm from aperture center. FIG. 5C illustrates a rectangular obscuration mask 8 mm wide located 9.5 mm from aperture center and at a 20 degree angle from the vertical when installed. It will be understood that embodiments of the present inventive concept are not limited to the mask configurations of FIGS. 5A through 5B and that these Figures are provided as examples only.

Figure 6A:
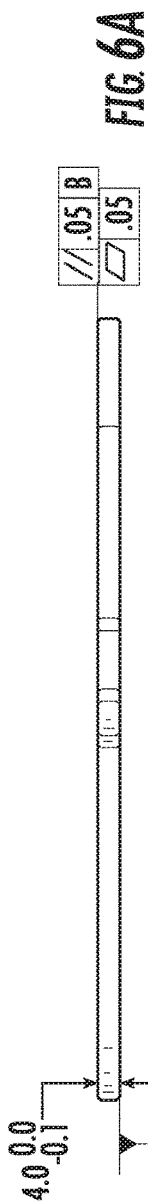
FIGS. 6A through 6C are diagrams illustrating a specific form of a non-circularly symmetric field diaphragm in accordance with some embodiments of the present inventive concept.
Figure 6B:
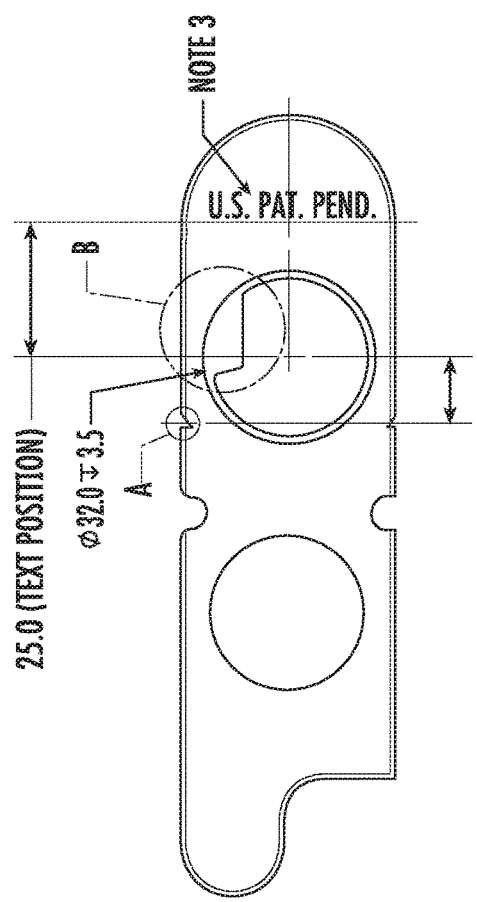
Figure 6C:
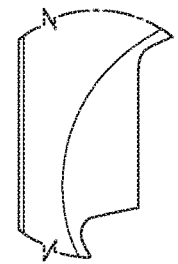

In particular, further embodiments in accordance with the present inventive concept are illustrated in FIGS. 6A through 6C. FIGS. 6A through 6C illustrated a hybrid between the bar and the tab mask, referred to herein as a partial bar, and is designed to provide more obscuration than the tab while seeking to reduce ray blockage in the full bar configuration that may block rays that are not otherwise contributing to glare. Various form factors for glare masks may be used having many other shapes and sizes without departing from the scope of the present inventive concept.

An approximation for the reduction in aperture of the field diaphragm of the glare mask may be considered as follows. As shown in FIG. 3B, the glare originates in rays emanating from the edge of the field diaphragm that have a maximum angle of incidence of impingement on the microscope objective. When the microscope objective is axially displaced, this marginal ray or rays traverses from the edge of the objective towards the center, and reflected from the surface of the objective escapes from the obscuration of the fold mirror and becomes a potentially offending glare ray.

Figure 7:
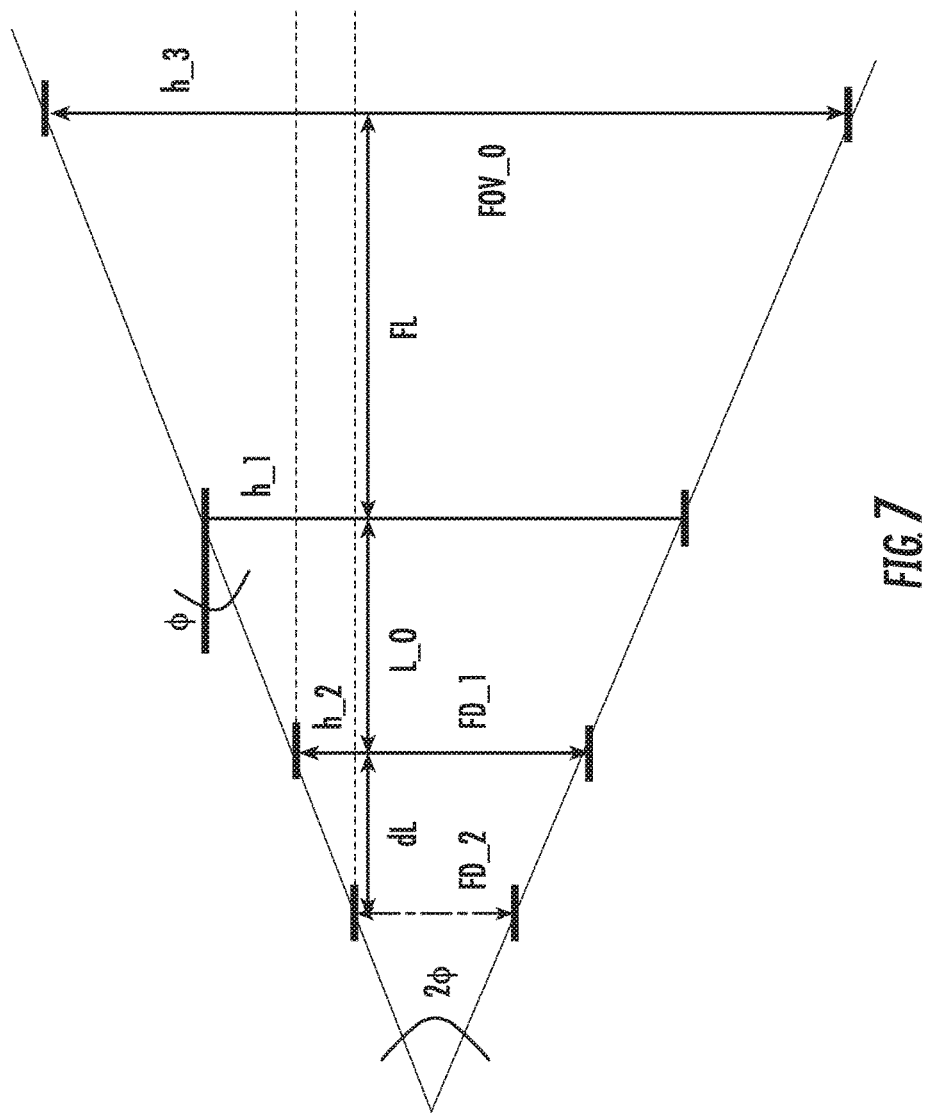
FIG. 7 is diagram illustrating a representation of a geometry applied to determine a radius of a meridian of a second field diaphragm that will inhibit glare, given knowledge of a first field diaphragm, path lengths from a first field diaphragm to the field of view, and displacement of an objective lens giving rise to new components of glare-inducing reflections in accordance with some embodiments of the present inventive concept.

An appropriate glare mask increased the likelihood that when the objective lens is displaced, the new marginal ray emanating from the new glare-reducing field diaphragm stays within the boundaries of the original marginal rays of the lens in its original position. Referring now to FIG. 7, a diagram illustrating a representation of a geometry applied to determine a radius of a meridian of a second field diaphragm that will inhibit glare, given knowledge of a first field diaphragm, path lengths from a first field diaphragm to the field of view, and displacement of an objective lens giving rise to new components of glare-inducing reflections in accordance with some embodiments of the present inventive concept will be discussed.

As illustrated in FIG. 7, FD_1 is diameter of the original field diaphragm as measured along a meridian of the marginal ray (the ray most likely to cause glare when the lens is displaced). The field diaphragm FD_1 is positioned a distance L_0 (including folds) from the surface of the microscope objective of focal length FL. With the objective in this position, the illuminated field of view is a diameter of FOV_0, representing a magnification M=FOV_0/FD_1. In some embodiments of the present inventive concept, FD_1 has a diameter 30 mm, the FOV with a 175 mm focal length lens is 55 mm, M=55/30=1.83 with the objective lens displaced a distance dL=60 mm, and the new field diaphragm FD_2 is positioned a new distance dL+L_0 from the objective lens. As illustrated, in order for the new marginal ray to stay within the glare-free bounds of the original system deployment, the new margin ray should stay within the trajectory of the original marginal ray, and the diameter of the field diaphragm FD_2 along the offending meridian should be within the illumination cone of angle 2*φ. With known quantities FD_1, L_0, FL, and FOV_1, the diameter FD_2 of the new field diaphragm along the offending meridian may be estimated by the following equation:

$$FD\_2=FD\_1-2*h\_2 \qquad \text{Eqn. 1}$$

where FD_2 is the diameter of the new field diaphragm, FD_1 is the diameter of the field diaphragm and where:

$$h\_2=h\_1*(dL/L\_0) \qquad \text{Eqn. 2}$$

where dL is the axial displacement of the microscope objective and $$h\_1=m*L\_0 \qquad \text{Eqn. 3}$$

where m is the slope of the marginal ray measured from the optical axis (note: m is not equal to magnification M) and in is represented by the following equation:

$$m=(FOV\_1-FD\_1)/[2*(L\_0+FL)]. \qquad \text{Eqn. 4}$$

The relationship between the diameters of field diaphragm 1 and field diaphragm 2 may be restated as follows:

$$FD\_2=FD\_1*[1-(M-1)*dL/(L\_0+FL)] \qquad \text{Eqn. 5}$$

Finally, that the diameter (or radius) of the second field diaphragm is de-magnified by a ratio R relative to the original field diaphragm as:

$$R=[1-(M-1)*dL/(L\_0+FL)] \qquad \text{Eqn. 6}$$

It will be understood that the de-magnification of the field diaphragm is a function of the magnification M of the original illumination optics, the original distance between the field diaphragm and the imapge plane L_0+FL, and the subsequent axial displacement of the objective lens dL.

In some embodiments of the present inventive concept, FL=175 mm; L_0=100 mm; FD_1=30 mm; FOV_1=55 mm; M=1.833; m=0.045 mm$^{-1}$; and dL=60 mm. Thus, using these variable in the equations set out above, FD_2=24.5 mm and $$FOV\_2=M*FD\_2=45 \text{ mm} \qquad \text{Eqn. 7}$$

where FOV_2 is the new field of view along the direction of the offending meridian in the image plane. Note that the mask need not be circularly symmetric, and a minimum field of illumination reduction R=FOV_2/FOV_1 need only occur along an imaged meridian that corresponds to glare-inducing marginal rays and, therefore, it is further useful to consider only a merdian radius along an offending direction, such that a radius along at least one merdian is related to the radius of the original field diaphragm according to:

$$FR\_2=FR\_1-h\_2 \qquad \text{Eqn. 8}$$

where FR_2 is a minimum radius along a critical meridian of the glare mask, or second field diaphragm and FR_1=FD_1/2 is the radius along the same meridian of the first field diaphragm.

Figure 8E:
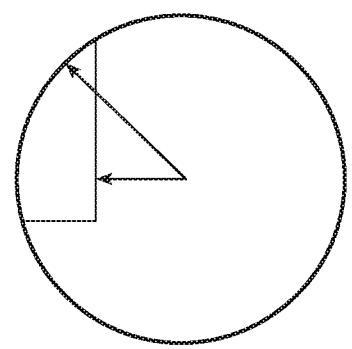
FIGS. 8C through 8E are diagrams illustrating non-circularly symmetric field diaphragms having a reduced radius along at least one meridian suitable for reducing asymmetric glare after displacement of an objective lens in accordance with some embodiments of the present inventive concept.
Figure 8B:
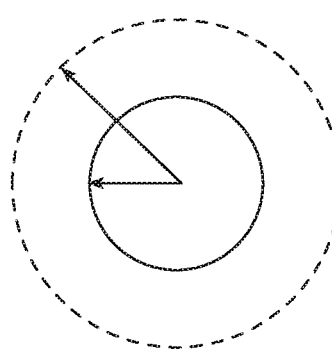
FIG. 8B is a diagram illustrating a radius of a circularly-symmetric second field diaphragm suitable for reducing glare after displacement of an objective lens in accordance with some embodiments of the present inventive concept.
Figure 8D:
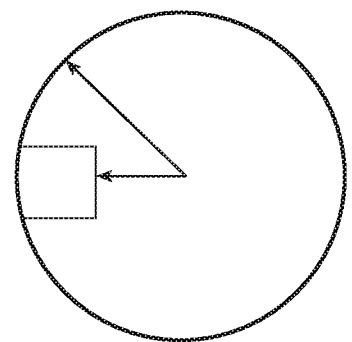
Figure 8A:
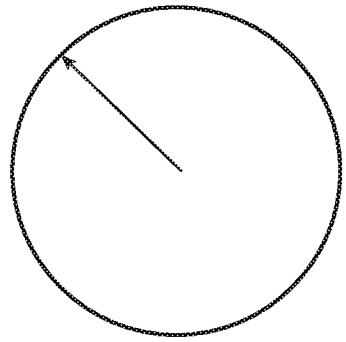
FIG. 8A is a diagram illustrating a radius of a meridian of a first field diaphragm in accordance with some embodiments of the present inventive concept.
Figure 8C:
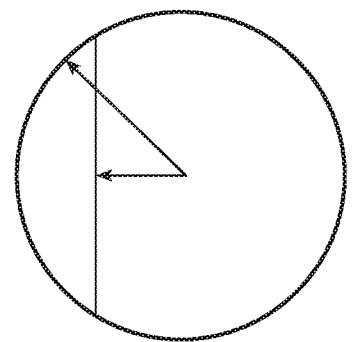

Referring now to FIGS. 8A through 8E, FIG. 8A is a diagram illustrating an original field diaphragm; FIG. 8B is a diagram illustrating a circularly symmetric glare mask or second field diaphragm with a reduced meridianal radius; FIG. 8C is a diagram illustrating a non-symmetric bar glare mask or second field diaphragm with a reduced meridianal radius; FIG. 8D is a diagram illustrating a non-symmetric tab glare mask or second field diaphragm with a reduced meridianal radius; and FIG. 8E is diagram illustrating a non-symmetric half-bar glare mask or second field diaphragm with a reduced meridianal radius.

The field diaphragm FD_2 is oriented such that marginal rays from the edge of the field diaphragm along a meridian of minimum diameter that reflect from a surface of the objective lens reflect outside of the acceptance angle for relay through any ocular channel of the microscope.

The masks discussed herein have opaque obscurations. It will be understood that opacity is not a definitive requirement. The obscurations may be such that ray randomization is sufficient to reduce or eliminate the impact of glare, such as with a ground-glass obscuration. Alternatively, the obscuration may deflect the offending marginal rays without attenuating them. Other ways to create a glare mask may be envisioned that obscuration that acts to remove marginal rays by using a glare mask along the delivery path of the illumination.

As discussed briefly above, the addition of an accessory to the infinity space of a surgical microscope alters the glare management strategy for the microscope illumination system. Thus, embodiments of the present inventive concept provide glare masks (field diaphragm masks) having various form factors that may be installed in a surgical microscope. These glare masks reduce or eliminate glare originating from the modified location of the main objective lens and have very little impact to the field of illumination at the subject (patient) plane.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

What is claimed is:

1. A field diaphragm for use in a surgical microscope, the field diaphragm positioned along, an optical axis of a microscope illumination system, the field diaphragm comprising:
   a stationary frame portion configured to be received by the surgical microscope; and
   a non-circularly symmetric mask portion integrated with the frame portion, the non-circularly symmetric mask portion positioned such that marginal rays from an edge of the field diaphragm along a meridian of minimum diameter that reflect from a surface of an objective lens of the microscope are blocked and are not relayed through any ocular channel of the microscope,
   wherein the mask portion comprises a circularly symmetric diaphragm with a non-circularly symmetric inset obscuration having a reduced meridianal radius relative to a meridianal radius of the circularly symmetric diaphragm; and
   wherein the inset obscuration comprises a rectangular obscuration mask being about 8 mm wide and located about 9.5 mm from a center of the field diaphragm and about twenty degrees from vertical.

2. The field diaphragm of claim 1, wherein the surgical microscope includes an accessory in an infinity space of the surgical microscope, presence of the accessory altering a glare management system of the surgical microscope by displacing a position of an objective lens of the surgical microscope.

3. The field diaphragm of claim 2, wherein the mask portion is configured to block portions of an illumination beam to reduce back reflections from the displaced objective lens.

4. A system fir controlling glare in oculars of a surgical microscope, the system comprising:
   a surgical microscope; and
   a stationary, non-circularly symmetric field diaphragm configured to be received by the surgical microscope, the non-circularly symmetric field diaphragm configured to block portions of an illumination beam of the surgical microscope to reduce regions of glare in a field of view (FOV) of the microscope visible through oculars thereof,
   wherein the system further comprises a circularly symmetric field diaphragm, wherein the non-circularly symmetric field diaphragm is configured to have a reduced meridianal radius relative to a meridianal radius of the circularly symmetric field diaphragm; and
   wherein the non-circularly symmetric field diaphragm comprises an inset obscuration having a rectangular obscuration mask being about 8 mm wide and located about 9.5 mm from a center of the field diaphragm and about twenty degrees from vertical.

5. The system of claim 4, wherein the surgical microscope further comprises an objective lens and an infinity space above the objective lens, the infinity space being configured to receive an accessory therein and presence of the accessory altering a glare management system of the surgical microscope by displacing a position of the objective lens of the surgical microscope.

6. The system of claim 5, wherein the non-circularly symmetric field diaphragm is configured to block portions of the illumination beam to reduce back reflections from the displaced objective lens.

7. The system of claim 5, wherein the accessory comprises an optical coherence tomography (OCT) accessory.

8. The system of claim 4, wherein the field diaphragm comprises:
   a frame portion configured to be received by the surgical microscope; and
   a mask portion integrated with the frame portion, the mask portion configured to block portions of the illumination beam of the surgical microscope.

* * * * *

UNITED STATES PATENT AND TRADEMARK OFFICE
CERTIFICATE OF CORRECTION

PATENT NO. : 10,409,046 B2
APPLICATION NO. : 14/935545
DATED : September 10, 2019
INVENTOR(S) : Christopher Saxer et al.

Page 1 of 1

It is certified that error appears in the above-identified patent and that said Letters Patent is hereby corrected as shown below:

In the Claims

Column 11, Line 25, in Claim 1, change "along," to -- along --.

Column 12, Line 8, in Claim 4, change "fir" to -- for --.

Signed and Sealed this
Fifteenth Day of October, 2019

Andrei Iancu
*Director of the United States Patent and Trademark Office*